US00PP28628P3

(12) United States Plant Patent
Summers

(10) Patent No.: US PP28,628 P3
(45) Date of Patent: Nov. 14, 2017

(54) RED WATERCRESS PLANT NAMED 'RW1'

(50) Latin Name: ***Nasturtium officinale* W.T. Aiton**
Varietal Denomination: RW1

(71) Applicant: B&W Quality Growers, LLC, Fellsmere, FL (US)

(72) Inventor: William L. Summers, Vero Beach, FL (US)

(73) Assignee: B&W Quality Growers, LLC, Fellsmere, FL (US)

( * ) Notice: Subject to any disclaimer, the term of this patent is extended or adjusted under 35 U.S.C. 154(b) by 228 days.

(21) Appl. No.: 13/998,262

(22) Filed: Oct. 15, 2013

(65) Prior Publication Data

US 2014/0101808 P1 Apr. 10, 2014

Related U.S. Application Data

(63) Continuation of application No. 12/611,276, filed on Nov. 3, 2009, now abandoned.

(60) Provisional application No. 61/111,247, filed on Nov. 4, 2008.

(51) Int. Cl.
*A01H 5/12* (2006.01)
*A01H 5/10* (2006.01)

(52) U.S. Cl.
USPC ..... Plt./258
CPC ..... *A01H 5/10* (2013.01)

(58) Field of Classification Search
USPC ..... Plt./258
See application file for complete search history.

(56) References Cited

U.S. PATENT DOCUMENTS

PP6,383 P 11/1988 Whitcomb

OTHER PUBLICATIONS

Shoukas Red is the New Green. Specialty Food Apr. 1, 2011, retrieved on Jul. 8, 2015, retrieved from the Internet at <www.specialtyfood.com/news/article/red-new-green/> 6 pp.*
Crowe, Francis D., 1998. PBR Application for Watercress "Vicred". Plant Varieties Journal 11(2):50 Australia.

* cited by examiner

*Primary Examiner* — June Hwu
(74) *Attorney, Agent, or Firm* — Vobach IP Law, LLC

(57) ABSTRACT

The present invention relates to a new and distinct variety of watercress plant, and its plant parts, including the mutation of an allele of watercress designated "BWRW", which results in watercress plants with red-pigmented leaves and/or stems. The red-green variety is distinguished from green watercress varieties, in particular with its red pigmentation ranging from dark purple to purple-grey to dark red to pink leaves and stems; intermediate-sized stem diameter ranging from 3.5 mm to 5.5 mm, which is commercially acceptable for both fresh and cooked consumption; a higher than average nutritional antioxidant capacity as measured by Ferric Reducing Ability of Plasma (FRAP) assays; as well as expanded harvesting seasons, with suitability to be grown in the United States year-round.

8 Drawing Sheets

Latin name of the genus and species of the plant claimed: The genus and species of the watercress variety of this invention is botanically identified as *Nasturtium officinale* W.T. Aiton.

Variety denomination: The variety denomination is 'RW1'.

BACKGROUND OF THE INVENTION

The present invention relates to a new and distinct variety of watercress plant and its plant parts, including the mutation of an allele of watercress designated "BWRW", which results in watercress plants with red-pigmented leaves and/or stems.

Watercress is also known as *Nasturtium officinale* W.T. Aiton and it belongs to the family Brassicaceae (formerly the Cruciferae family). Watercress is native to Europe and Asia, common in Great Britain and widely naturalized in the United States and Canada. It has also been introduced into the West Indies and South America. It is reported that Nicholas Messier first grew watercress in Erfurt, Germany in the middle of the 16th century. English cultivation started in the early 1800s, when a farmer near London began to grow watercress for use in salads. It was not long before its popularity spread. Today the crisp green sprigs of watercress are commonly eaten out of hand, combined with other tender greens in salads and used as a garnish on hot and cold dishes.

The foregoing examples of the related art and limitations related therewith are intended to be illustrative and not exclusive. Other limitations of the related art will become apparent to those of skill in the art upon a reading of the specification.

BRIEF SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

The following traits have been repeatedly observed and represent the characteristics of the new and distinct variety of red watercress plant named 'RW1'. These traits in combination distinguish this variety from all other commercial varieties known to the inventor.

1. A plant with green venation and red pigmentation of leaves and/or stems, with red coloration ranging from dark purple to purple-grey to dark red to pink;
2. An average intermediate-sized stem diameter of 3.5 to 5.5 mm, which is commercially acceptable for both fresh and cooked consumption;
3. A nutritional antioxidant capacity of at least 2.27 times greater than compared green watercress varieties; and
4. Expanded harvest season, with suitability to be grown in the United States year-round.

Plants of the present invention have not been observed under all possible environmental and cultural conditions. The phenotype will vary somewhat with variations in environmental conditions, for example, with fluctuation in temperature and photoperiod, without, however, any variance in genotype.

According to the invention, there is provided a new and distinct variety of red watercress plant named 'RW1', and its plant parts, including its mutant allele designated "BWRW". This invention thus relates to the watercress which comprises a mutant allele which results in red-pigmentation on leaves and/or stems.

In another aspect, the present invention provides regenerable cells for use in tissue culture. The tissue culture will preferably be capable of regenerating plants having the physiological and morphological characteristics of the foregoing watercress plant, and of regenerating plants having substantially the same genotype as the foregoing watercress plant. Still further, the present invention provides watercress plants regenerated from the tissue cultures of the invention.

In addition to the exemplary aspects and embodiments described above, further aspects and embodiments will become apparent by study of the following descriptions.

BRIEF DESCRIPTION OF THE DRAWINGS

The accompanying photographs labeled

FIG. 1 shows the first plant specimen, demonstrating dominant dark-purple pigmented leaves and dark reddish-green stems. The more uniform pigmentation occurrence on plant structures is more typical of fall and winter months, or in areas with a shortened photoperiod.

FIG. 2 shows a section of the stem of the first plant specimen, demonstrating dark-purple to deep-reddish-green pigmentation and leaves with significant red pigmentation and green veins.

FIG. 3 shows a closely cropped image of the first plant specimen with red and green coloration of a section of the stem and leaves with significant red pigmentation, and green veins.

FIG. 4 shows a plant leaf from the first plant specimen, demonstrating dominant red pigmentation on the blade with distinctly green veins.

FIG. 5 shows the second plant specimen, demonstrating green colored stems and mostly green leaves with red pigmentation mainly distributed on leaf borders. The broadened green coloration on plant structures is more typical of summer months, or in areas with a lengthened photoperiod.

FIG. 6 shows the second plant specimen with green stem and green leaves with scarce red pigmentation mainly distributed on leaf borders.

FIG. 7 shows a closely cropped image of the second plant specimen with green stem and green leaves with scarce red pigmentation mainly distributed on leaf borders.

FIG. 8 shows an image of a leaf from the second plant specimen, demonstrating significant green coloration on the blade with scarce red pigmentation mainly distributed on leaf borders.

FIG. 9 is a representation of a silique illustrating the characteristics detailed in the specification.

FIG. 10 is a representation of a seed illustrating the characteristics detailed in the specification.

FIG. 11 is a representation of a raceme illustrating the characteristics detailed in the specification.

FIG. 12 is a representation of a flower illustrating the characteristics detailed in the specification.

FIG. 13 is a representation of a flower petal illustrating the characteristics detailed in the specification.

FIG. 14 is a representation of the calyx illustrating the characteristics detailed in the specification.

FIG. 15 is a representation of the gynoecium illustrating the characteristics detailed in the specification.

FIG. 16 is a representation of the androecium illustrating the characteristics detailed in the specification.

DEFINITIONS

Figure 1:
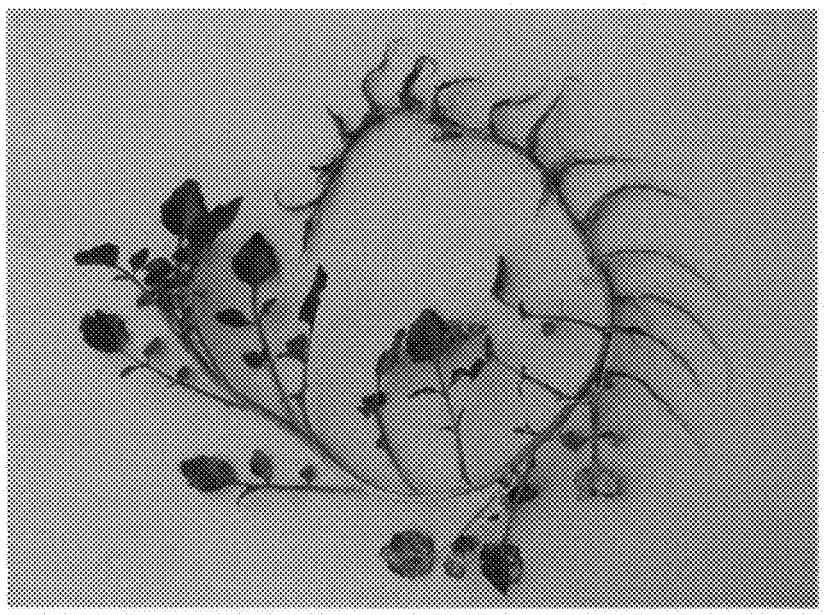
FIGS. 1 through 8 show two typical specimens of the leaves and stems of the new variety demonstrating the pigmentation variation produced by the mutant allele designated BWRW. The photographs were taken of four-week-old harvested plants from different locations in the same bed and photographed indoors under fluorescent lighting in the Fall of 2015. The different specimens demonstrate the variation in pigment distribution as occurs with variations in environmental conditions, such as exposure to day length or photoperiod.
Figure 2:
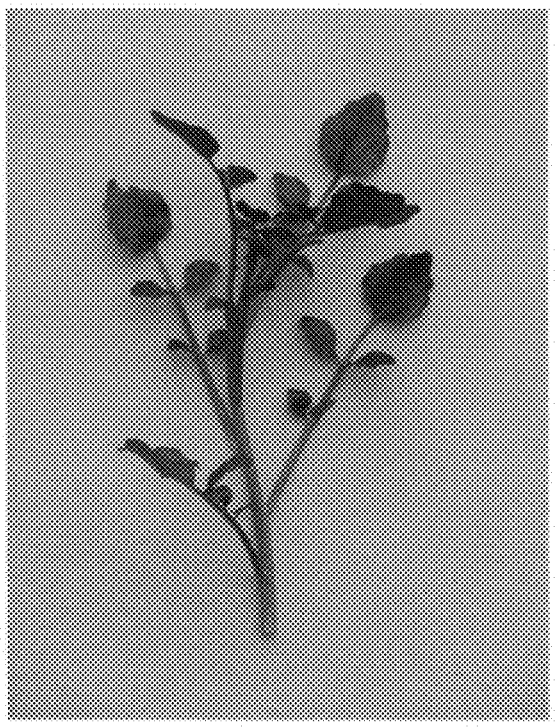
Figure 3:
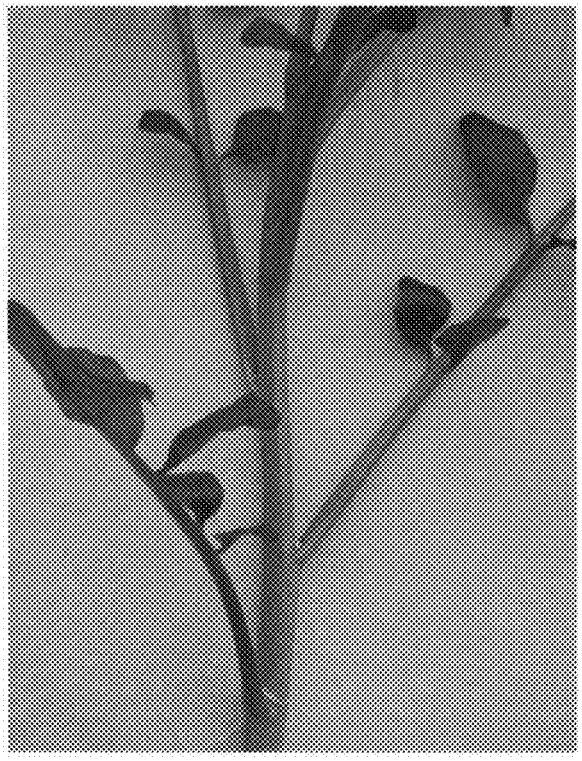
Figure 4:
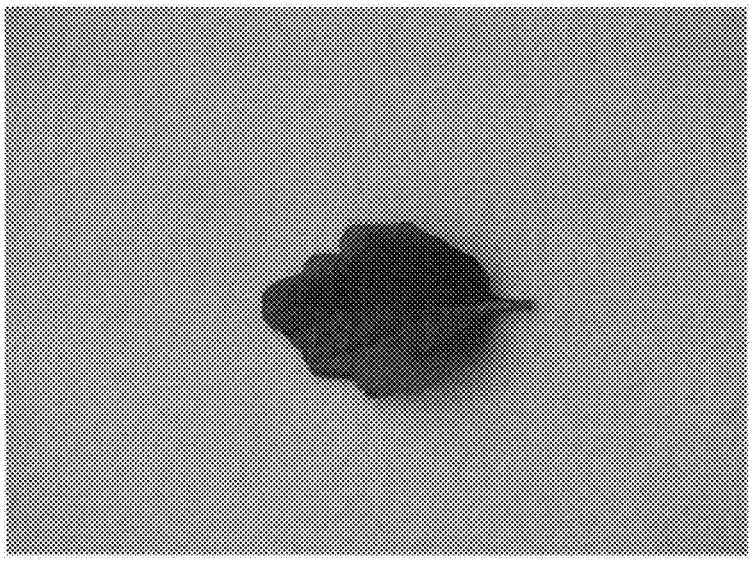
Figure 5:
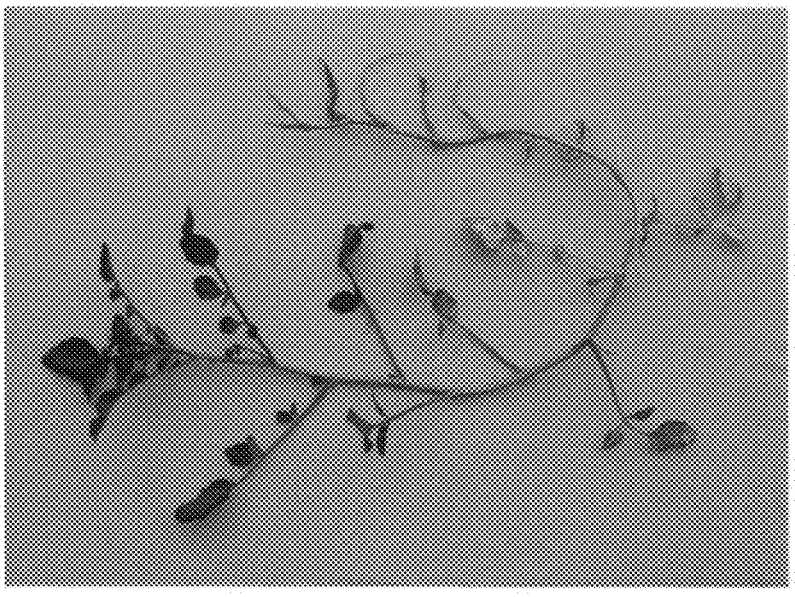
Figure 6:
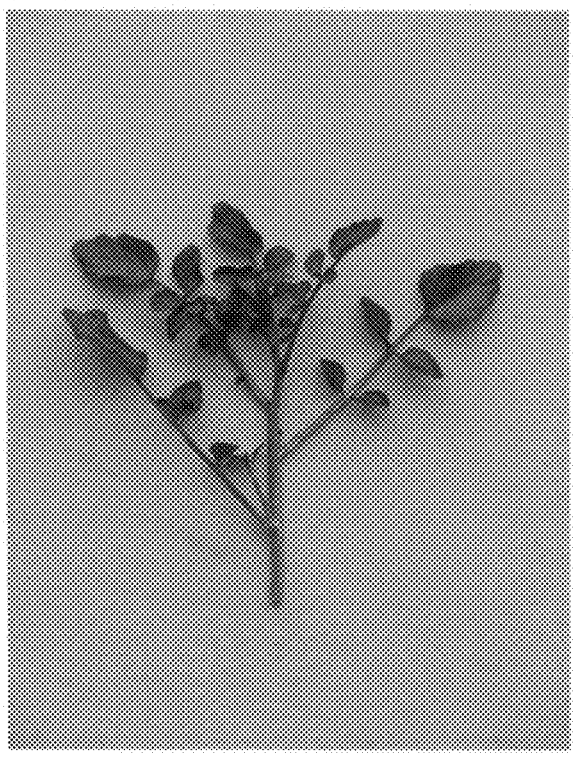
Figure 7:
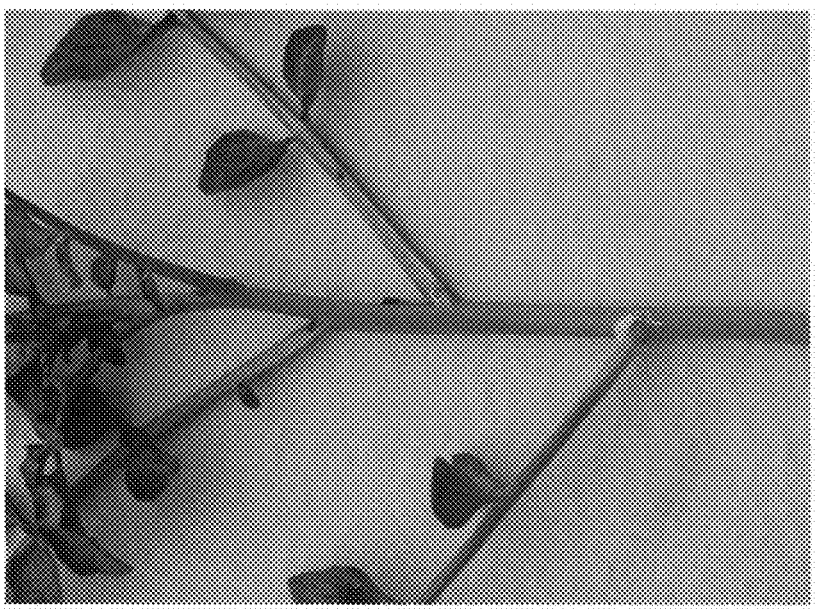
Figure 8:
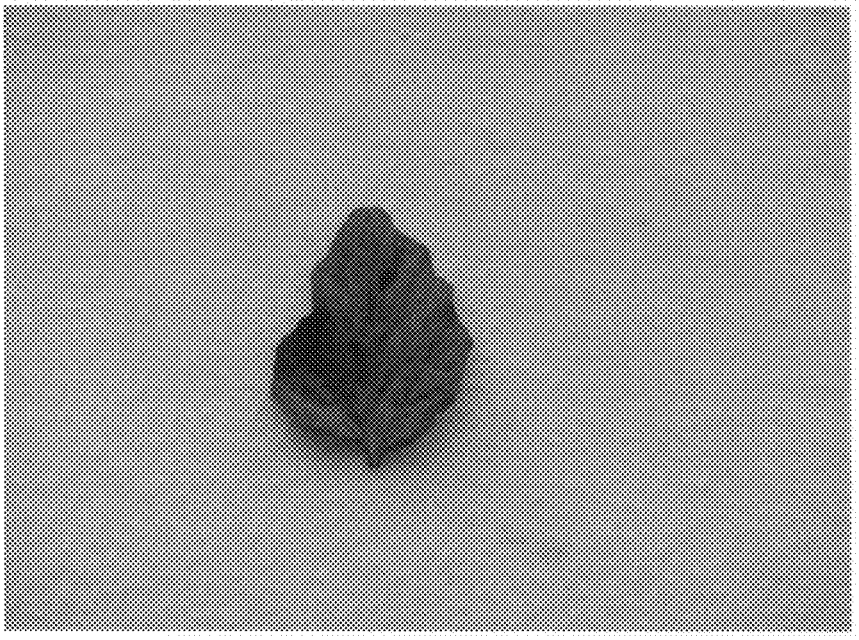
Figure 9:
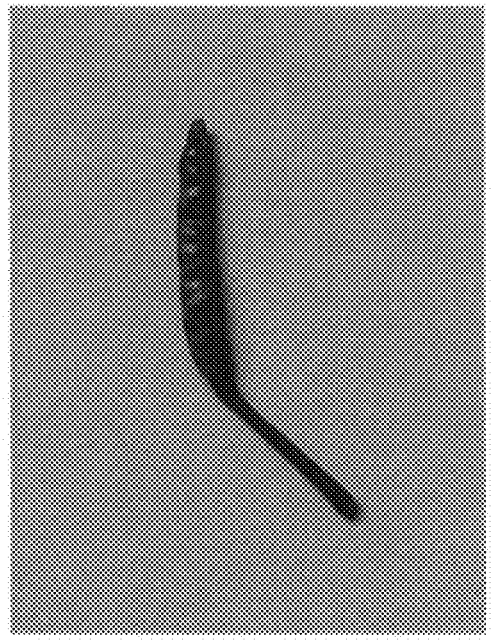
FIGS. 9 through 16 demonstrate the typical reproductive characteristics of flowers, siliques, and seeds. Photographs were taken indoors under fluorescent lighting in the Summer of 2016. The 8-10-week-old plants were grown in a field bed in Martinsburg, W. Va.
Figure 10:
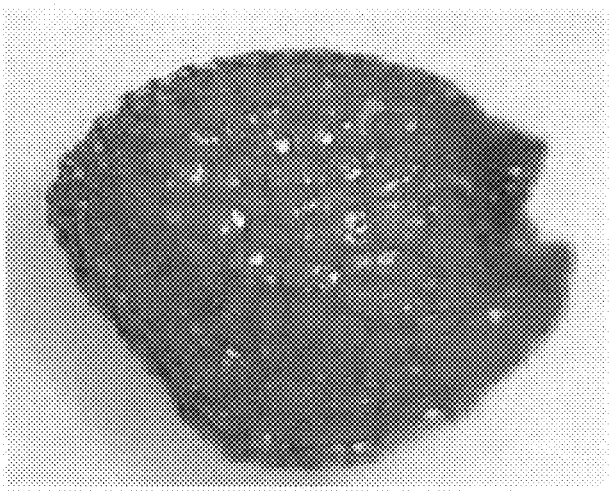
Figure 11:
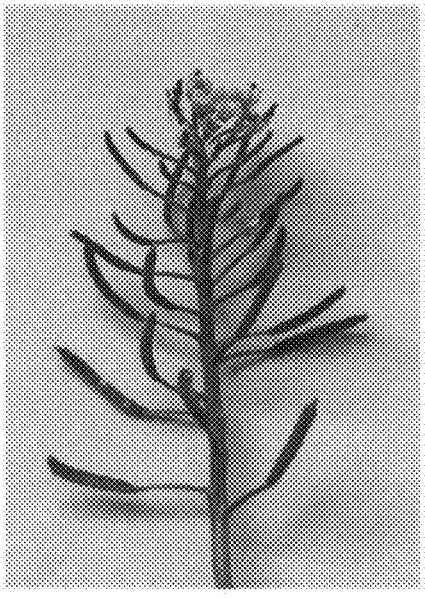
Figure 12:
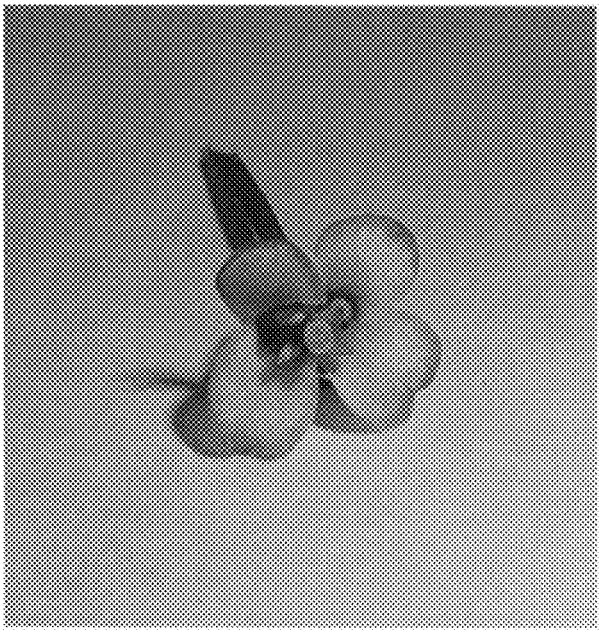
Figure 13:
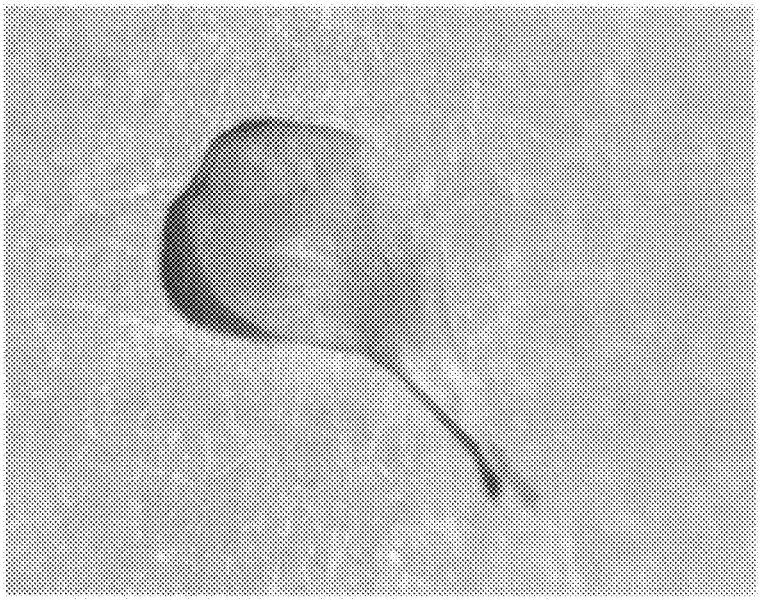
Figure 14:
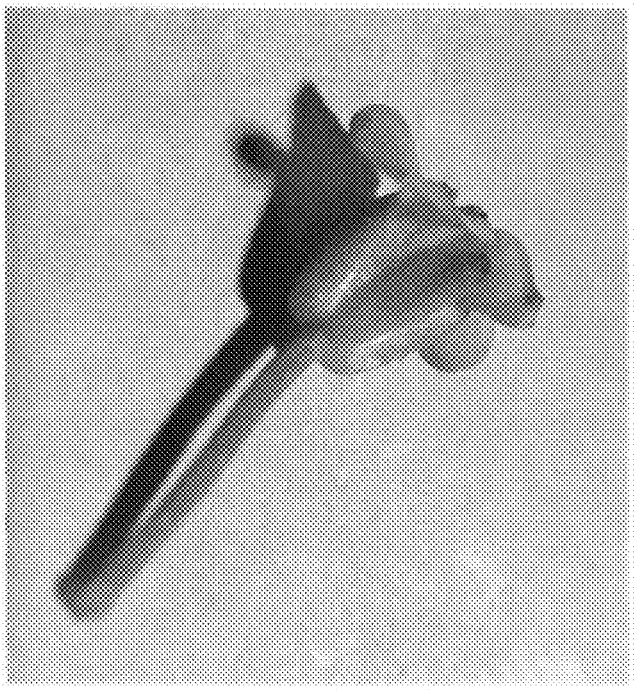
Figure 15:
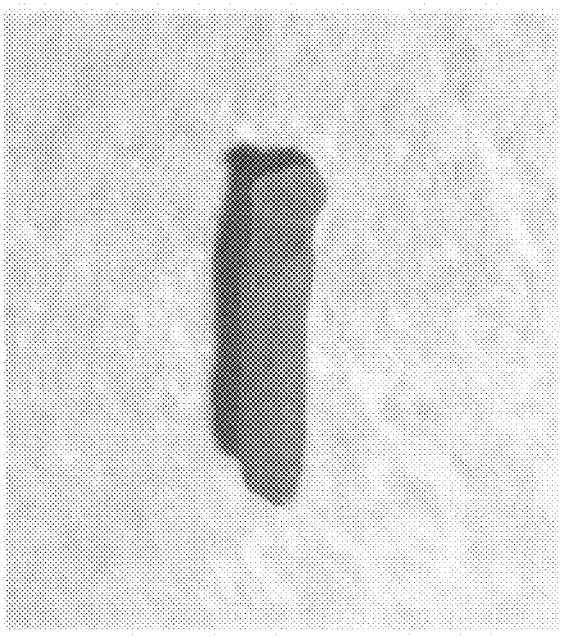
Figure 16:
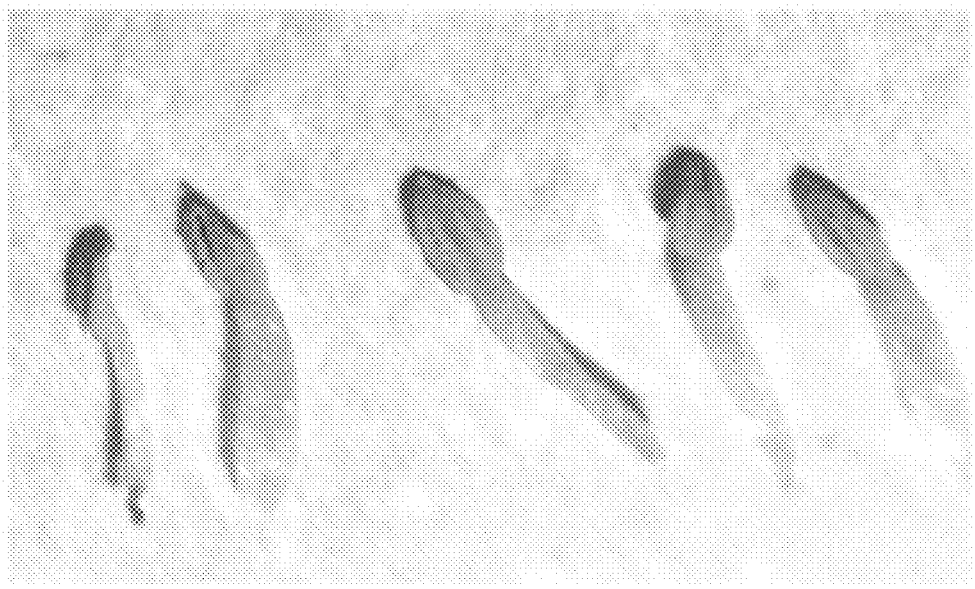

In the description and tables that follow, a number of terms are used. In order to provide a clear and consistent understanding of the specification and claim, the following definitions are provided:

Allele. An "allele" is any of one or more alternative form of a gene (dominant or recessive), all of which alleles relates to one trait or characteristic gene.

BWRW. "BWRW" refers to the mutant allele or alleles of the present invention that results in red-pigmented leaves in the watercress plant named 'RW1'.

Essentially all the physiological and morphological characteristics. A plant having "essentially all the physiological and morphological characteristics" means a plant having the physiological and morphological characteristics, except for the characteristics derived from the converted gene or genes.

Regeneration. "Regeneration" refers to the development of a plant from tissue culture.

Yield. The term "Yield" is typically defined when used. Yield can mean the number of bunches of watercress per acre where, on average, 4 bunches equal approximately a pound. Alternatively, if watercress is harvested loose, yield may be measured in pounds (lbs) or kilograms (Kg) per acre.

DETAILED BOTANICAL DESCRIPTION

The present invention relates to a new and distinct variety of red watercress plant and its plant parts, including the mutation of allele designated "BWRW" in the genus *Nasturtium* that is phenotypically described in the present invention via a watercress plant having red-pigmented leaves and/or stems.

Watercress is a perennial plant and is generally produced for human consumption. Watercress is typically grown in rectilinear beds with flowing water and the beds are tested frequently for the presence of harmful pathogens. The flowing water may flow through the bed and exit or it may be re-circulated to flow through multiple times. Companies may also add a proprietary blend of fertilizer elements to the irrigation water in the flow-through system. Each bed will have a base to support watercress root growth. The base composition may be natural soil, which is commonly used in the United States, soil overlaid with pebbles, which is commonly used in England, or various plastic compounds overlaid with a more porous material that roots can hook on to.

Watercress is often used to make tea or to make a stock base for cooking. It is also frequently used in place of lettuce on sandwiches. More recently chefs have begun offering watercress in salads and the red-pigmented watercress provides chefs and other food preparers with a striking color option when adding watercress to typically green salads. In addition, members of medical research communities in the U.S. and U.K. have begun detailing the varied anticancer properties of watercress.

The present invention provides a mutant allele designated "BWRW" which results in watercress plants having red-pigmented leaves and/or stems. The red pigmentation of the leaves can range in appearance from dark purple and dark red to pink depending on the environmental conditions and whether one is looking at the upper or lower surface of the leaf.

In addition to conferring the red pigment to the leaves and/or stems, the BWRW allele also affects the distribution of the pigment in the leaves depending on the maturity of the crop and variation in the environmental conditions such as with fluctuations of photoperiod during different times of the year. The red color is distributed mainly in the leaf blade while the veins remain bright green under a short photoperiod (less than 10 h), and for example, when grown in Florida where temperatures fluctuate between 30° and 50° F. during cooler months. In growing conditions under a long photoperiod (longer than 10 h), for example in northern latitudinal areas where temperatures range between 89° and 105° F., the red color is distributed largely at the leaf margins while the veins and the leaf blades are bright green.

Discovery and Propagation of 'RW1'

The mutant allele of the embodiments of the present invention, BWRW, unexpectedly arose as a spontaneous mutation in a population of triploid green watercress grown in New Market, Ala. during the Summer of 2006. The Alabama farm located at 34°55'0.51"N 86°25'2.63"W, 230 m elevation above the sea level has a production area of 26 acres. In the 1940s, there were many small watercress farms in New Market and in nearby towns, but today the farm where the present invention was discovered, is the only remaining farm. The green watercress varieties, such as Green Watercress U.S. Standard (referenced in Tables 2 and 3) were cultivated in the same location and are still in production today. During 2006, a small area of the farm was designated for the yield evaluation of potential watercress crosses. The red watercress was also cultivated with arugula (30% of the land area) but arugula is no longer cultivated at the New Market farm.

Prior to the present invention, a red-pigmented leaf mutation of this type in watercress was unknown. The single, large, mutant plant was moved from Alabama to Fellsmere, Fla. and placed in a research bed during the Winter-Spring season of 2006-2007. The line was expanded in 8'×40' beds for five generations through asexual reproduction via stem cuttings under the direction of the inventor.

The line was then uprooted and transferred between Alabama and Florida for further reproduction during growing seasons lasting for periods of 6 months each. The line was expanded via stem cuttings for five generations in the Summer season (2007), for five generations in the Winter-Spring season (2007-2008), for four generations in the Summer season (2008), and for one generation in the Winter-Spring season (2008-2009). In total, twenty generations of the invention were employed by Spring 2009. Additionally, the 'RW1' line is maintained through a tissue culture program to maintain healthy plants free of pests and pathogens. Tissue culture is now the preferred method of asexual propagation.

To successfully propagate via stem cuttings, a land area (or bed) is prepared prior to planting. The land is tilled, leveled, and then water added to flow from one side to the other. The cuttings are then placed on beds with the thin water layer. Watercress cuttings are taken from long stems averaging 40 to 75 cm length and are never blooming at this growth stage. Vegetative cuttings produce more plants when the cuttings are placed horizontally onto the beds. Buds located in nodes start growing after the cutting is planted on beds. Rooting from nodes produces successful plant establishment. Some of the roots are submerged in water but others grown under the soil layer and the base of shoot are submerged in water but the major shoot is above water.

Typically the first crop reaches a harvestable stage in about 7 weeks with subsequent harvests occurring at 4 to 5 week intervals depending on environmental conditions. Harvest can occur by hand making a bunch in the field and placing a rubber band around the bunch and trimming the end to the desired length.

Morphological Description

The red-pigmented watercress of the present invention has shown uniformity and stability for red-pigmented leaves and/or stems and other traits substantially as shown and described herein, within the limits of environmental influence for pigmentation. The line has been increased through at least 20 crop cycles since 2006 with continued observation for uniformity. Presently, plants of the invention encompass 10 to 15% of the 26 acre cultivated area. No variant traits have been observed or are expected in the present invention. The color determinations are in accordance with the Fifth Edition (2007) of The Royal Horticultural Society Colour Chart published by The Royal Horticultural Society (London, England), except where general color terms of ordinary dictionary significance are used. The following characteristics were taken of four-week-old plants, with the exception of the flowers, siliques, and seeds, which were collected from eight-to-ten-week old plants. The red-pigmented watercress of the present invention has the following morphologic and other characteristics.

TABLE 1

VARIETY DESCRIPTION

Plant: A perennial succulent temperate herb

Stems: Appearance: Floating and semi-erect stems, typically stays under water while 17.78 cm (7.0 in) turns upward when ready for harvest
Diameter: 3.5 to 5.5 mm diameter at 17.145 cm (6.75 in) from apical meristem
Internode length: 1.27 cm (0.5 in)
Surface texture: Cylindrical and succulent with a brilliant cuticle and smooth surface
Color: TABLE 1A
Table Description: Stem color determined for contrasting red watercress types defined generally as "purple" type and "green-red" type show slight differences in color pattern due to photoperiods of different growing seasons.

| Plant | Stem | |
|---|---|---|
| section | Purple (Winter) | Green-Red (Summer) |
| Immature | Yellow green 144A | Yellow green 144B |
| Mature (6 inches from tip) | Yellow green 144A | Yellow green 144B |

Leaves:
Arrangement: A compound leaf with two opposite pair of oval leaflets and a pentagon shaped terminal leaflet
Apex: Moderately apiculate
Base: Inequilateral truncate to round
Margin: Crenate to sinuate
Size of terminal leaflet (the largest leaf from an average derived from 20 plants):
Green-red leaves: Length: 41.0 mm: Width: 37.0 mm
Purple leaves: Length: 35.0 mm: Width: 28.0 mm
Size of leaflet (average derived from 20 plants):
Green-red leaves: Length: 19.0 mm: Width: 14.0 mm
Purple leaves: Length: 16.0 mm: Width: 12.0 mm
Number of leaflet per leaf (average): Two opposed leaflet pairs or three pairs in rare occurrence
Leaflet surface texture:
Upper Surface: Glabrous
Lower Surface: Rugose
Color:

TABLE 1B

Leaf color determined for contrasting red watercress types defined generally as "purple" type and "green-red" type show differences in color pattern due to photoperiods of different growing seasons.

| | | | Leaf | | |
|---|---|---|---|---|---|
| | Plant section | | Purple (Winter) (30° to 50° F., or 10 hour photoperiod or less) | | Green-Red (Summer) (89° to 105° F., or long photo-period) |
| Immature | Upper side (blade) | Main | Greyed purple 186A | Main | Green 143A |
| | | Veins | Green 143A | Edges | Greyed purple 186B |

TABLE 1B-continued

Leaf color determined for contrasting red watercress types defined generally as "purple" type and "green-red" type show differences in color pattern due to photoperiods of different growing seasons.

| | | | | | |
|---|---|---|---|---|---|
| | Lower side (opposite) | Main | Purple 77A | Main | Green 143A |
| | | Veins | Green 143A | Edges | Purple 77A |
| Mature (6 inches from tip) | Upper side (blade) | Main | Greyed purple 186A | Main | Green 143A |
| | | Veins | Green 143A | Edges | Greyed purple 186B |
| | Lower side (opposite) | Main | Purple 77A | Main | Green 143A |
| | | Veins | Green 143B | Edges | Purple 77A |

Petiole
Length (average distance from the stem to the first leaflet pairs):
Green-red. Length: 41.0 mm; Width: 37.0 mm
Purple: Length: 35 mm; Width: 28 mm
Surface texture:
Upper surface: Semi cylindrical shape (cross section) and succulent with a brilliant cuticle and smoothly surface
Lower surface: None as petiole is semi cylindrical
Color:
Green-red. RHS 144B (yellow green)
Purple: RHS 144A (yellow green)

Inflorescence: Plant is typically harvested prior to flowering
Appearance: Raceme
Raceme Size (average): Up to 200.0 mm
Number of flowers per raceme (average): 3 to 7 well opened flowers and15 to 24 unopened flowers
Floral cycle: One flower/seed production cycle during summer and winter per floral induction treatment
Flower:
Size (average): Radial diameter of 4.0 to 6.0 mm
Type or form (of flower): Dissymmetric or slightly zygomorphic (cross-like arrangement)
Number of petals per individual flower: 4
Petal shape: Clawed free petals
Petal apex type: Rounded
Petal margin: Entire
Flower Color: White RHS 155B and purple RHS 77A
Calyx:
Size (average in mm): 2.0 to 3.5 mm
Sepal shape: Saccate sepals, oblong shaped and tip obtuse
Color: Yellow-green, RHS 146C
Pedicel:
Length (average): 5.0 to 7.0 mm
Surface texture: Pedicel is semi-circular. The convex side is glabrous and flat side has dense hair
Color: Green RHS 146A
Peduncle:
Length (average): 10.0 to 15.0 mm
Surface texture: Smooth between nodes, plain hairs around nodes
Color: Green RHS 143A Reproductive Organs:
Gynoecium:
Size (average): 2.0 to 4.5 mm
Number per flower (average): 1
Color: Yellow-green RHS 146A and yellow-green RHS 153B TABLE 1B-continued

| Leaf color determined for contrasting red watercress types defined generally as "purple" type and "green-red" type show differences in color pattern due to photoperiods of different growing seasons. |
|---|
| Androecium: |
| Size (average): 2.6 to 4.5 mm |
| Number per flower (average): 6 |
| Color: Yellow-green RHS 144D and yellow-green RHS 152D |
| Fruit (silique): |
| Shape: Linear cylindrical silique |
| Size (average, mm): 6.0 to 10. 0 mm |
| Color: Yellow-green RHS 144A |
| Seed: |
| Quantity: 42 to 60 seeds per silique but only 6 to 10 develop fully |
| Shape: Obovate |
| Texture: Reticulated |
| Color: Greyed-orange, RHS 175A and RHS165B |

COMPARISON TO SIMILAR VARIETIES

Tables

Watercress plants grow as long indeterminate stems which may elongate in a prostrate or upright orientation. Prostrate forms usually root into support media at the axils while simultaneously producing a lateral stem which orients upright for harvest. Upright forms bend upright forming an L shape without long prostrate runs. Unexpectedly, the red watercress plant named 'RW1', containing the BWRW mutant allele of the present invention presents an intermediate form, grows more slowly than standard green watercress, and produces 36% fewer marketable stem bunches than standard 3n or 2n green watercress lines. Table 2 shows the yield of the red watercress plant named 'RW1', containing the BWRW mutant allele of the present invention as compared to the yield of standard green watercress plants. In Table 2, column 1 shows the type of watercress, column 2 shows the ploidy, column 3 shows the year, columns 4 through 12 show the yield in bunches per acre and column 13 shows the mean yield for each year.

TABLE 2

Comparison of Red Watercress Plant Named 'RW1' Containing the BWRW Mutant Allele with Standard Green Watercress Lacking the BWRW Mutant Allele for Yield over Two Years Four Week Periods Beginning January 1

| Watercress Line | Ploidy | Year | 1 | 2 | 3 | 4 |
|---|---|---|---|---|---|---|
| Red Watercress Plant Named 'RW1' | 3n | 2008 | 18,800 | 12,770 | 16,529 | 7,336 |
| | | 2009 | 15,750 | 13,730 | 19,226 | 15,270 |
| Green Watercress USA Standard | 3n | 2008 | 21,732 | 23,823 | 25,354 | 22,850 |
| | | 2009 | 16,151 | 25,353 | 22,588 | 23,979 |
| Green Watercress UK Standard | 2n | 2008 | 18,257 | 18,782 | 20,862 | 21,674 |
| | | 2009 | 27,433 | 26,269 | 18,401 | 20,982 |

TABLE 2-continued

Comparison of Red Watercress Plant Named 'RW1' Containing the BWRW Mutant Allele with Standard Green Watercress Lacking the BWRW Mutant Allele for Yield over Two Years Four Week Periods Beginning January 1

| Watercress Line | Year | 5 | 6 | 11 | 12 | 13 | Mean |
|---|---|---|---|---|---|---|---|
| Red Watercress Plant Named 'RW1' | 2008 | 16,592 | 15,771 | | 15,520 | 11,919 | 14,405 |
| | 2009 | 8,996 | | | | | 14,594 |
| Green Watercress USA Standard | 2008 | 27,303 | 22,900 | 21,495 | 21,223 | 18,795 | 22,841 |
| | 2009 | 25,228 | 23,196 | | | | 22,749 |
| Green Watercress UK | 2008 | 26,828 | 21,234 | | 15,808 | 17,800 | 20,156 |
| | 2009 | | | | | | 23,271 |

As shown in Table 2, the red watercress plant named 'RW1', containing the mutant allele BWRW of the present invention unexpectedly yielded significantly fewer bunches per acre than either the standard U.S. or U.K. green watercresses which lack the BWRW mutant allele. Importantly, while slower growth reduces the total number of bunches and crops per season, slower growth allows the crop to hold longer in the field before going out of market specifications. An additional benefit is that individual stems do not develop as large an undesirable central hole as faster growing lines do.

Watercress stem diameters affect how watercress is used by consumers. Watercress can be consumed fresh as a lettuce substitute or in a mix of fresh greens; it can be boiled, sautéed or stir-fried. Watercress lines marketed for fresh consumption typically possess a smaller stem diameter, for example in the U.K. where watercress is most often consumed fresh, the standard stem diameter is 2.33 mm. Watercress lines marketed for stir fry, boiling, or sautéing possess larger stem diameters of 3.5 to 5.5 mm. Unexpectedly, the red watercress plant named 'RW1', containing the BWRW mutant allele of the present invention had a mean stem diameter that was intermediate between the green standard U.S. watercress line and the green standard U.K. watercress line.

Table 3 shows the mean stem number per bunch, the mean weight per stem, and the mean stem diameter for red watercress plant named 'RW1', which contains the BWRW mutant allele of the present invention as compared to standard U.S. and U.K. green watercresses which lack the BWRW mutant allele. Also included are two experimental green watercresses, 47-8 and 96-1, which lack the BWRW mutant allele of the present invention. In Table 3 column 1 shows the watercress line, column 2 shows the ploidy of each line, column 3 shows the growing location, column 4 shows the date the watercress was cut and the measurements taken, column 5 shows the mean stem number per bunch, column 6 shows the mean weight in grams per stem, column 7 shows the mean stem diameter in millimeters, and column 8 shows the standard deviation of the stem diameter in millimeters.

TABLE 3

Comparison of Various Stem Characteristics between Red Watercress Plant Named 'RW1', Containing the BWRW Mutant Allele and Standard Green Watercress and Two Experimental Watercress Lines

| Watercress Line | Ploidy | Location | Cut Date | Mean Stem # per Bunch |
|---|---|---|---|---|
| Red Watercress Plant Named 'RW1' | 3n | Florida | Jan. 12, 2009 | 34 |
| Red Watercress Plant Named 'RW1' | 3n | Tennessee | Jun. 5, 2009 | 49 |
| Green Watercress US Standard | 3n | Florida | Jan. 12, 2009 | 42 |
| Green Watercress US Standard | 3n | Tennessee | Jun. 5, 2009 | 45 |
| Green Watercress UK Standard | 2n | Florida | Jan. 14, 2009 | 91 |
| 47-8 | 6n | Florida | Jan. 12, 2009 | 44 |
| 47-8 | 6n | Tennessee | Jun. 5, 2009 | 32 |
| 96-1 | 6n | Florida | Jan. 12, 2009 | 28 |
| 96-1 | 6n | Tennessee | Jun. 5, 2009 | 48 |

| Watercress Line | Mean Wt per Stem (g) | Mean Stem Diameter (mm) | Stem Diameter, Std Dev (mm) |
|---|---|---|---|
| Red Watercress Plant Named 'RW1' | 4.68 | 4.39 | 1.11 |
| Red Watercress Plant Named 'RW1' | 4.14 | 3.58 | 1.26 |
| Green Watercress US Standard | 3.59 | 3.60 | 1.09 |
| Green Watercress US Standard | 4.63 | 4.06 | 1.22 |
| Green Watercress UK Standard | 1.57 | 2.33 | 0.76 |
| 47-8 | 3.48 | 3.39 | 1.02 |
| 47-8 | 6.64 | 5.37 | 1.27 |
| 96-1 | 5.99 | 4.46 | 1.11 |
| 96-1 | 4.86 | 3.86 | 1.10 |

As shown in Table 3, the red watercress stem diameter, 3.58 to 4.39 mm, compares favorably with the U.S. standard 3n line, 3.6 to 4.06 mm, and with two new experimental hexaploid lines.

The red watercress plant named 'RW1', containing the BWRW mutant allele of the present invention unexpectedly can be grown in the U.S. in summer because its stem diameter range of 3.5 to 5.5 mm is commercially acceptable for a variety of uses by consumers. The stem diameter of the red watercress containing the BWRW mutant allele of the present invention is such that it is not too small to be used for stir-fry, boiling and sautéing nor is it too big to be used for fresh consumption. As shown in Table 3, the BWRW allele allows watercress to be grown year-round unlike the standard green U.K. watercress.

The assay Ferric Reducing Ability of Plasma (FRAP) is considered an assay of antioxidant power. In tests at the University of South Hampton, U.K., watercress FRAP values of a number of watercress lines were tested and ranged from 1.61 to 5.65 nmol Fe 2+ equivalents per gram fresh weight. In these tests red watercress plant named 'RW1', containing the BWRW mutant allele of the present invention had an unexpected FRAP value of 5.65 nmol which is at least 2.27 times greater than the mean of 2.27 nmol Fe 2+ equivalents per gram fresh weight generated for green watercress lines which lack the BWRW mutant allele. This means the red watercress plant named 'RW1' has greater antioxidant power than standard green watercress lines.

What is claimed is:

1. A new and distinct variety of watercress plant having the characteristics as illustrated and described herein.

* * * * *